(12) United States Patent
Li et al.

(10) Patent No.: US 12,673,135 B2
(45) Date of Patent: Jul. 7, 2026

(54) COLLAGEN-BASED MENISCUS IMPLANTS

(71) Applicant: Collagen Matrix, Inc., Oakland, NJ (US)

(72) Inventors: Shu-Tung Li, Wyckoff, NJ (US); Natsuyo Shishido Lee, Basking Ridge, NJ (US)

(73) Assignee: Collagen Matrix, Inc., Oakland, NJ (US)

( * ) Notice: Subject to any disclaimer, the term of this patent is extended or adjusted under 35 U.S.C. 154(b) by 0 days.

(21) Appl. No.: 17/554,134

(22) Filed: Dec. 17, 2021

(65) Prior Publication Data

US 2022/0105239 A1 Apr. 7, 2022

Related U.S. Application Data

(62) Division of application No. 15/680,700, filed on Aug. 18, 2017.

(51) Int. Cl.

| | |
|---|---|
| *C07K 1/14* | (2006.01) |
| *A61L 27/24* | (2006.01) |
| *A61L 27/36* | (2006.01) |
| *A61L 27/56* | (2006.01) |
| *A61L 27/58* | (2006.01) |
| *C07K 14/78* | (2006.01) |
| *A61L 2/081* | (2026.01) |
| *A61L 103/05* | (2026.01) |

(52) U.S. Cl.
CPC ........... *A61L 27/24* (2013.01); *A61L 27/3612* (2013.01); *A61L 27/3654* (2013.01); *A61L 27/3687* (2013.01); *A61L 27/56* (2013.01); *A61L 27/58* (2013.01); *C07K 1/145* (2013.01); *C07K 14/78* (2013.01); *A61L 2/081* (2013.01); *A61L 2103/05* (2026.01); *A61L 2430/06* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 4,880,429 | A | 11/1989 | Stone |
| 5,306,311 | A | 4/1994 | Stone et al. |
| 5,681,353 | A | 10/1997 | Li et al. |
| 5,984,858 | A | 11/1999 | Stone |
| 5,993,844 | A | 11/1999 | Abraham et al. |
| 6,042,610 | A | 3/2000 | Li et al. |
| 6,046,379 | A | 4/2000 | Stone et al. |
| 6,599,524 | B2 | 7/2003 | Li et al. |
| 7,309,359 | B2 | 12/2007 | Trieu et al. |
| 7,807,192 | B2 | 10/2010 | Li et al. |
| 8,956,411 | B2 | 2/2015 | Ingham et al. |
| 9,308,219 | B2 | 4/2016 | Li et al. |
| 2005/0221703 | A1 | 10/2005 | Stone |
| 2010/0152852 | A1 | 6/2010 | Ingham et al. |
| 2011/0014153 | A1 | 1/2011 | Derwin et al. |
| 2012/0022233 | A1 | 1/2012 | Breiter et al. |
| 2012/0064043 | A1 | 3/2012 | Ferguson et al. |
| 2013/0172999 | A1 | 7/2013 | Kaplan et al. |
| 2015/0216664 | A1 | 8/2015 | Ingham et al. |
| 2015/0344842 | A1* | 12/2015 | Sheu ................... A61L 27/3633 435/378 |

OTHER PUBLICATIONS

Azhim et al. ('Preparation of decellularized meniscal scaffolds using sonication treatment for tissue engineering' 35th annual international conference of the IEEE EMBS, 2013 pp. 6953-6956). (Year: 2013).*

Norzarini et al. ('Decellularized bovine meniscus in morphological assessment prior to bioscaffold preparation' IEEE Xplore 2015 pp. 1-4). (Year: 2015).*

Chen et al. "Current Advances in the Development of Natural Meniscus Scaffolds: Innovative Approaches to Decellularization and Recellularization" Cell and Tissue Research vol. 370, pp. 41-52, 2017.

Cheung "Distribution of Type I, II, III and V in the Pepsin Solubilized Collagens in Bovine Menisci" Connective Tissue Research vol. 16, pp. 343-356, 1987.

(Continued)

*Primary Examiner* — Ronald T Niebauer

(74) *Attorney, Agent, or Firm* — Merchant & Gould P.C.; Daniel J. Pereira

(57) ABSTRACT

A method for producing a collagen meniscus implant by obtaining a freshly excised non-human meniscus, rinsing it in an aqueous solution, drying the rinsed meniscus, shaping it to approximate in dimension an average-sized human meniscus, extracting non-collagenous material from the shaped meniscus, and sterilizing it, yielding a collagen meniscus implant containing at least 90% by weight of type I collagen, less than 0.5% by weight of glycosaminoglycan, and less than 600 ppm DNA. Also disclosed is a collagen meniscus implant prepared by the above method. Further provided is a biocompatible and bioresorbable porous implant for meniscus repair. The implant includes a three-dimensional network of collagen fibers oriented in a direction approximating the collagen fiber orientation of a human meniscus. The implant has a size and a contour substantially equivalent to a human meniscus, and has a chemical composition similar to the above-described collagen meniscus implant.

6 Claims, 5 Drawing Sheets

(56) References Cited

OTHER PUBLICATIONS

Eleswarapu et al "Tensile Properties, Collagen Content, and Crosslinks in Connective Tissues of the Immature Knee Joint" PLoS ONE vol. 6, pp. 1-7, 2011.

Fox et al "The Basic Science of Human Knee Menisci: Structure, Composition, and Function" Sports Health vol. 4, pp. 340-351, 2012.

Gendimenico et al "Diphenylamine-Colorimetric Method for DNA Assay: A Shortened Procedure by Incubating Samples at 50° C." Analytical Biochemistry vol. 173, pp. 45-48, 1988.

Klompmaker et al."Porous Polymer Implants for Repair of Full-Thickness Defects of Articular Cartilage: An Experimental Study in Rabbit and Dog" Biomaterials vol. 13, pp. 625-634, 1992.

Monllau et al "Outcome After Partial Medial Meniscus Substitution with the Collagen Meniscal Implant at a Minimum of 10 Years' Follow-Up" Anthroscopy: The Journal of Anthroscopic and Related Surgery vol. 27, pp. 933-943, 2011.

RCM6 Resorbable Collagen Membrane—15×20mm printed Aug. 17, 2017.

Steadman et al "Tissue-Engineered Collagen Meniscus Implants: 5-to 6-Year Feasibility Study Results" Anthroscopy: The Journal of Anthroscopic and Related Surgery vol. 21, pp. 515-525, 2005.

Toyonaga et al "Substitute Meniscus of Teflon-Net for the Knee Joint of Dogs" Clinical Orthopaedics and Related Research vol. 179, pp. 291-297, 1983.

Veth et al "Experimental Meniscal Lesions Reconstructed with a Carbon Fiber-Polyurethane-Poly(L-Lactide) Graft" Clinical Orthopaedics and Related Research vol. 202, pp. 286-293, 1986.

Dong, et al. "Application of Collagen Scaffold in Tissue Engineering: recent advances and new perspectives" Polymers, Version 8, pp. 1-20; 2016.

Aamodt, Joseph M. et al. "Extracellular Matrix-based Biomaterial Scaffolds and the Host Response." Biomaterials; vol. 86; 2016.

Zach, "Range vs. Standard Deviation: When to Use Each." Statology; 2023.

* cited by examiner

Prior Art

COLLAGEN-BASED MENISCUS IMPLANTS

CROSS-REFERENCE TO RELATED APPLICATIONS

The present application is a divisional of U.S. patent application Ser. No. 15/680,700 filed on Aug. 18, 2017, the content of which is hereby incorporated by reference in its entirety.

BACKGROUND

The meniscus is a crescent shaped fibrocartilage that is anatomically situated in the knee joint between the femoral condyle and the tibial plateau of the knee. See FIG. 1. Each knee contains a medial meniscus and a lateral meniscus. They act to disperse the weight of the body and reduce friction during movement.

Knee injuries frequently result in a tear of the meniscal tissue. In the clinic, torn meniscal tissue is either repaired by suture arthroscopically or removed. It is known that partial or total removal of a meniscus causes force concentration on the opposing articular cartilage and, in time, results in degenerative arthritis.

Reconstruction or replacement of the meniscus typically involves the use of allograft tissue. However, use of allograft tissue is limited by cost and availability, as well as by the possibility of disease transmission. In addition, meniscus allograft transplantation is typically indicated only for total or near total replacement of a damaged or missing meniscus. Meniscus allograft tissue has not been used routinely for partial or segmental meniscus reconstruction or replacement.

In an alternative approach, permanent or resorbable meniscus scaffolds have been developed to act as a template to regenerate damaged tissue. Yet, the materials used to construct these scaffolds, e.g., teflon, polyester, carbon fiber, and poly (L-lactide)-reinforced carbon fiber, cause progressive degenerative changes of the femoral and tibial articular cartilages, as well as chronic inflammation around the implanted scaffold. Meniscus repair implants made of segmented polyurethane elastomers have only recently been introduced into the clinic. This material has a long in vivo residence time, the long-term implications of which are not yet known.

Meniscus implants formed from highly purified and reconstituted bovine type I collagen fibrils have been in clinical use since the early 2000s. The use of this product typically necessitates a minimum of 8-12 weeks of rehabilitation time after implantation.

Recently proposed was a method of preparing a xenograft implant harvested from a non-human source for the treatment of human meniscus tear. However, xenografts in general are poorly accepted by humans due to bio-incompatibility. Additionally, non-human menisci are not suitable for direct implantation due to their size and shape mismatch.

The need exists for a collagen-based meniscus implant having optimized biochemical and biomechanical characteristics to prevent early failure of the implant from tear or dislodgement, to facilitate cell migration and growth into the implant, and to reduce rehabilitation time following implantation.

SUMMARY

To meet this need, a method for producing a collagen meniscus implant is disclosed. The method is carried out by obtaining a freshly excised non-human meniscus, rinsing it in an aqueous solution, drying the rinsed meniscus, shaping it to approximate in dimension an average-sized human meniscus, extracting non-collagenous material from the shaped meniscus, and sterilizing the extracted non-human meniscus, thereby forming the collagen meniscus implant. Carrying out the method yields a collagen meniscus implant containing at least 90% by weight of type I collagen, less than 0.5% by weight of glycosaminoglycan, and less than 600 ppm DNA.

Also disclosed is a collagen meniscus implant prepared by the above method.

A biocompatible and bioresorbable porous implant for meniscus repair is also encompassed by the invention. The implant includes a three-dimensional network of collagen fibers derived from a non-human meniscus. The collagen fibers are oriented in a direction approximating the collagen fiber orientation of a human meniscus, and the implant has a size and a contour substantially equivalent to a human meniscus. Further, the implant is at least 90% by weight of type I collagen and contains less than 600 ppm DNA and less than 0.5% by weight of glycosaminoglycan.

The details of one or more embodiments of the invention are set forth in the description and the drawings below. Other features, objects, and advantages of the invention will be apparent from the description and from the claims. All references cited herein are hereby incorporated by reference in their entirety.

BRIEF DESCRIPTION OF THE DRAWINGS

The description below refers to the accompanying drawings, of which.

DETAILED DESCRIPTION

Figure 1:
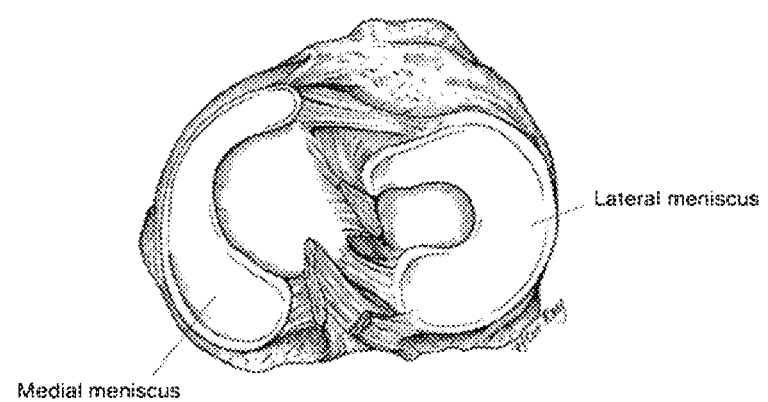
FIG. 1 is a drawing showing the top view of the menisci of the left knee joint of a human.

As mentioned above, a method is disclosed for preparing a collagen meniscus implant. First, a freshly excised non-human meniscus is obtained. The non-human meniscus can be bovine, porcine, ovine, canine, or equine meniscus. In a particular embodiment, the non-human meniscus is bovine meniscus.

The non-human meniscus is rinsed in an aqueous solution. The rinsing solution can be $H_2O$. The rinsing is performed to remove water-soluble proteins and blood components loosely associated with the meniscus tissue.

Following the washing step, the meniscus is dried. Drying can be carried out by, e.g., air drying and freeze-drying. In a specific method, the meniscus is freeze-dried to preserve the original shape and size of the meniscus. In a particular example, the meniscus is freeze-dried for 72 h at −10° C. at 80 mTorr.

After drying the meniscus, it is shaped to approximate in dimension an average-sized human meniscus. Referring to the left side of FIG. 2, the dimensions of a medial meniscus after shaping can be in the range of A=0.7-0.8 cm, B=3-4 cm, and H=0.5-0.6 cm. Referring to the right side of FIG. 2, the range of dimensions for a lateral meniscus after shaping can be A=0.7-0.8 cm, B=2.5-3.5 cm, and H=0.5-0.6 cm. In an embodiment, the dimensions can be customized to fit a particular individual patient. The shaping can be done manually, for example, with a scalpel or a razor blade. In another example, the shaping can be done using a hand-held power shaping tool. Alternatively, the shaping can be done by machine, e.g., a computer numerical control milling machine using computer-aided design software to properly dimension the meniscus.

During the shaping step, the meniscus is maintained at a low temperature to minimize denaturation of proteins therein. The temperature can be from −196° C. to 4° C. For example, the meniscus can be immersed in liquid $N_2$ periodically during the shaping procedure. In another example, the shaping is carried out in a cold room held at 4° C.

The shaped meniscus is then subjected to a series of extractions to remove non-collagenous material. The extractions are carried out at 4° C. by incubating the shaped meniscus in the following extraction solutions sequentially: (i) $H_2O$, (ii) an ionic detergent (e.g., sodium dodecylsulfate and 3-[(3-Cholamidopropyl)dimethylammonio]-1-propane-sulfonate), (iii) a non-ionic detergent (e.g., TRITON™ X-100), (iv) $MgCl_2$ or guanidine HCl, (v) $NaOH/Na_2SO_4$, (vi) $HCl/Na_2SO_4$, (vii) NaCl, (viii) isopropanol or ethanol, and (ix) $H_2O$. In an exemplary method, each incubation is carried out for 6-96 h. A skilled artisan would understand that the order of the above incubations can be changed while still achieving the goal of removing non-collagenous material from the shaped meniscus. Non-collagenous materials removed by the incubations include, but are not limited to, water-soluble protein, DNA, lipid, proteoglycan, and glycosaminoglycan (GAG).

Finally, the shaped, extracted meniscus is sterilized. Sterilization can be performed by methods known in the art, e.g., gamma irradiation. In an exemplary method, the shaped, extracted meniscus is freeze-dried prior to being sterilized. Alternatively, the gamma sterilization can be performed on a hydrated collagen meniscus implant.

The above method is free of any enzymatic digestion steps and any oxidizing steps.

As mentioned, supra, a collagen meniscus implant produced by the method of this invention is also disclosed. The implant contains at least 90% by weight of type I collagen (e.g., at least 91%, 92%, 93%, 94%, 95%, 96%, 97%, 98%, and 99%).

The collagen meniscus implant produced by the disclosed method also contains less than 600 ppm of DNA (e.g., less than 550 ppm, 500 ppm, 450 ppm, 400 ppm, 350 ppm, 300 ppm, 250 ppm, 200 ppm, 150 ppm, 100 ppm, and 50 ppm).

The implant also contains less than 0.5% by weight of GAG (e.g., less than 0.45%, 0.4%, 0.35%, 0.3%, 0.25%, 0.2%, 0.15%, 0.1%, and 0.05%).

Also described above is a biocompatible and bioresorbable porous implant for meniscus repair. The implant (i) includes a three-dimensional network of collagen fibers oriented in a direction approximating the collagen fiber orientation of a human meniscus, and (ii) has a size and a contour substantially equivalent to a human meniscus. The network of collagen fibers is derived from a non-human meniscus, e.g., bovine, porcine, ovine, canine, or equine meniscus. In an exemplary embodiment, the network of collagen fibers is derived from bovine meniscus.

The porous implant contains a plurality of pores having a void volume of at least 60% of the total implant volume (e.g., at least 65%, 70%, 75%, 80%, and 85%). The pores can have a size of 5 μm to 100 μm (e.g., 5 μm, 10 μm, 20 μm, 30 μm, 40 μm, 50 μm, 60 μm, 70 μm, 80 μm, 90 μm, and 100 μm). Preferably, the pores are large enough to accommodate cells therein. For example, the porous implant has pores large enough to permit fibrochondrocytes to migrate inside the implant after implantation. Over time, the fibrochondrocytes can form endogenous extracellular matrix to replace the three-dimensional network of collagen fibers provided by the biocompatible and bioresorbable porous implant.

The biocompatible and bioresorbable porous implant is stable in vivo after implantation for a period of 6 to 12 months (e.g., 6, 7, 8, 9, 10, 11, and 12 months).

The porous implant of the invention has a tensile strength greater than 500 $kg/cm^2$ (e.g., greater than 550 $kg/cm^2$, 600 $kg/cm^2$, 550 $kg/cm^2$, 550 $kg/cm^2$, 550 $kg/cm^2$, and 1000 $kg/cm^2$).

The porous implant also has a suture retention strength of greater than 2 kg (e.g., greater than 2.5 kg, 3.0 kg, 3.5 kg, 4.0 kg, 4.5 kg, 5.0 kg, 7.5 kg, and 10 kg).

Like the collagen meniscus implant described, supra, the biocompatible and bioresorbable porous implant is at least 90% by weight of type I collagen (e.g., at least 91%, 92%, 93%, 94%, 95%, 96%, 97%, 98%, and 99%).

The porous implant also contains less than 600 ppm of DNA (e.g., less than 550 ppm, 500 ppm, 450 ppm, 400 ppm, 350 ppm, 300 ppm, 250 ppm, 200 ppm, 150 ppm, 100 ppm, and 50 ppm).

The implant also contains less than 0.5% by weight of GAG (e.g., less than 0.45%, 0.4%, 0.35%, 0.3%, 0.25%, 0.2%, 0.15%, 0.1%, and 0.05%).

Without further elaboration, it is believed that the above description has adequately enabled the present invention. The following examples are, therefore, to be construed as merely illustrative, and not limitative of the remainder of the disclosure in any way whatsoever.

EXAMPLES

Example 1: Preparation of Collagen Meniscus Implants

Fresh medial menisci obtained from 3-6 month-old calves were first cleaned with scissors and scalpels to remove adherent tissues, followed by a thorough rinse with $H_2O$ to remove water-soluble proteins and blood containing moieties. The washed menisci were then freeze dried. Freeze-drying the washed menisci prior to machining was important for preserving their original size and shape. The freeze-drying also made the menisci rigid for easy handling and machine shaping. The freeze-dried menisci were each mechanically machined to the size and shape of an average human medial meniscus or lateral meniscus (see FIGS. 1 and 2), making sure that the surfaces of the machined menisci were preserved. Preservation of the surface is important for the implant to glide easily over the femoral condyles post-implantation.

Figure 2:
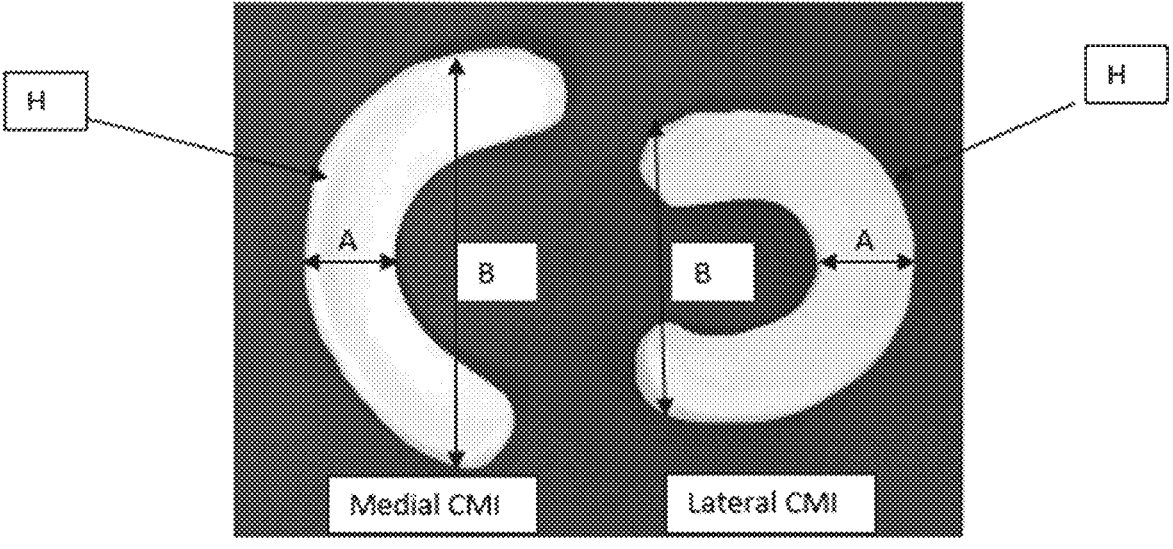
FIG. 2 is a photograph of two embodiments of the collagen meniscus implant of the invention. A=side-to-side dimension, B=tip-to-tip dimension, and H=height.
Figure 3A:
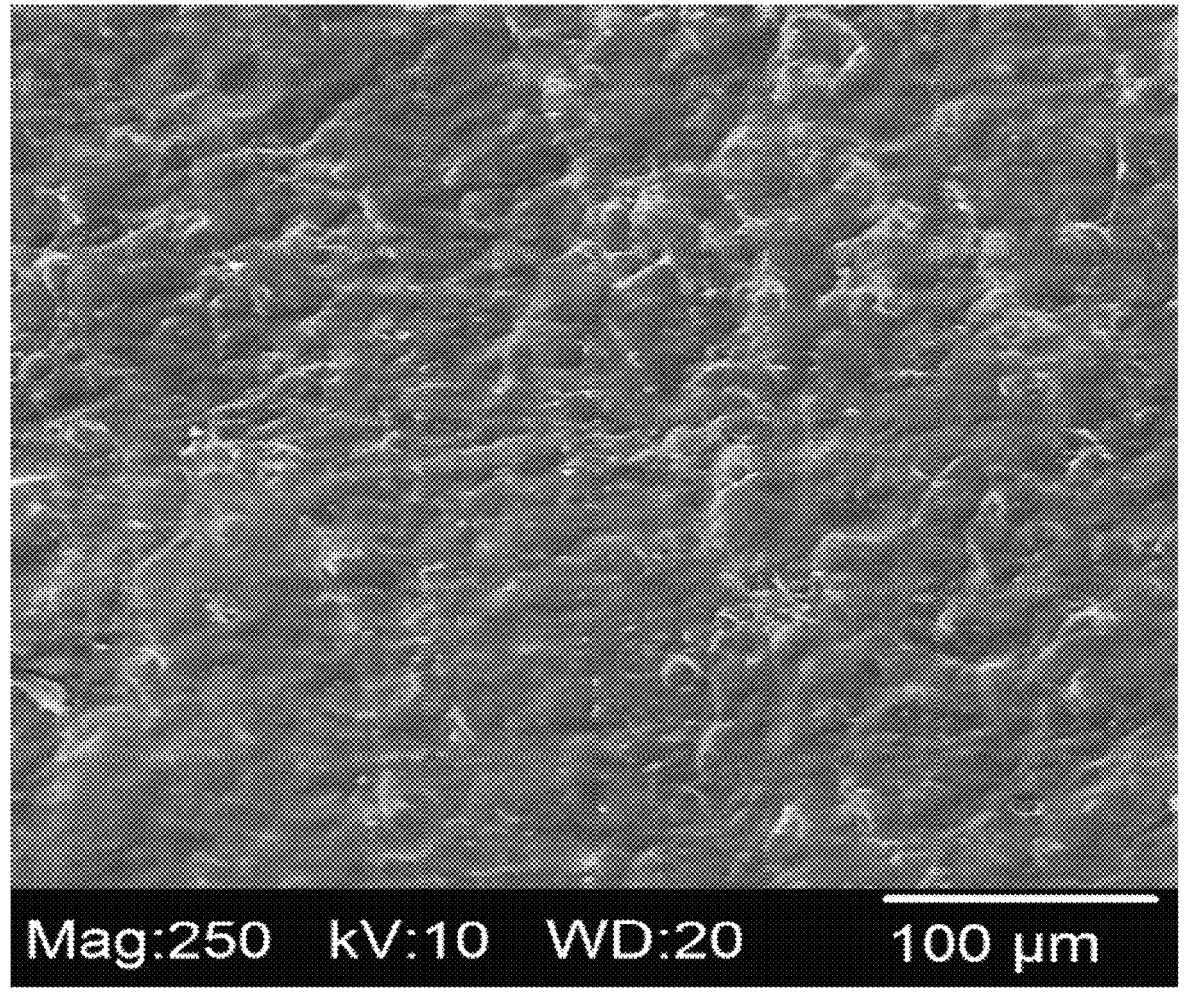
FIG. 3A is an electron micrograph of the top surface of the embodied collagen meniscus implant.
Figure 3B:
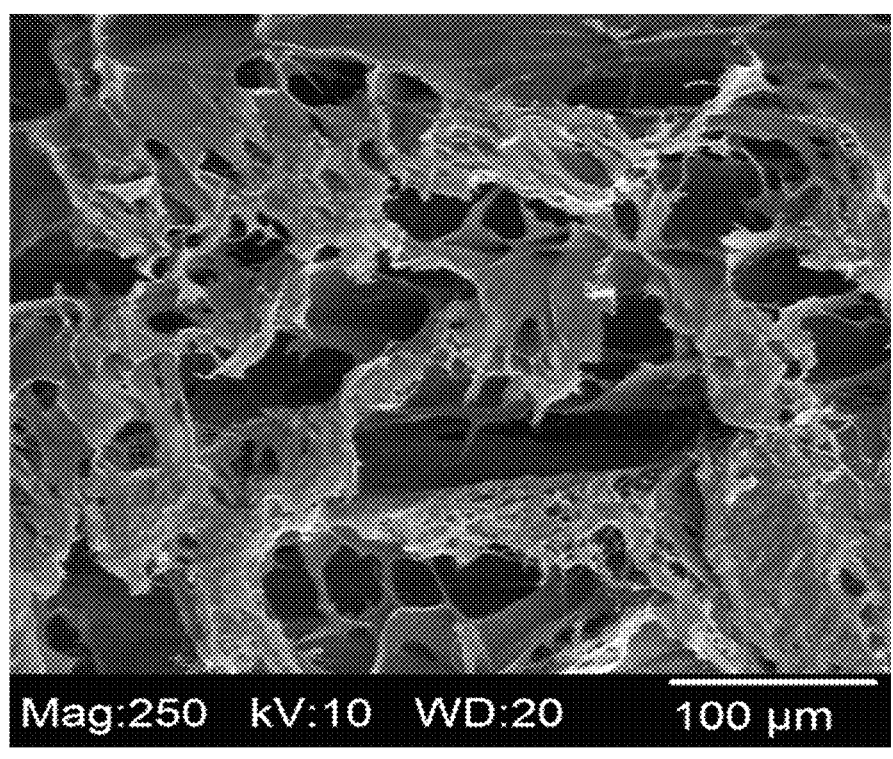
FIG. 3B is an electron micrograph of the outside perimeter surface of the embodied collagen meniscus implant.
Figure 3C:
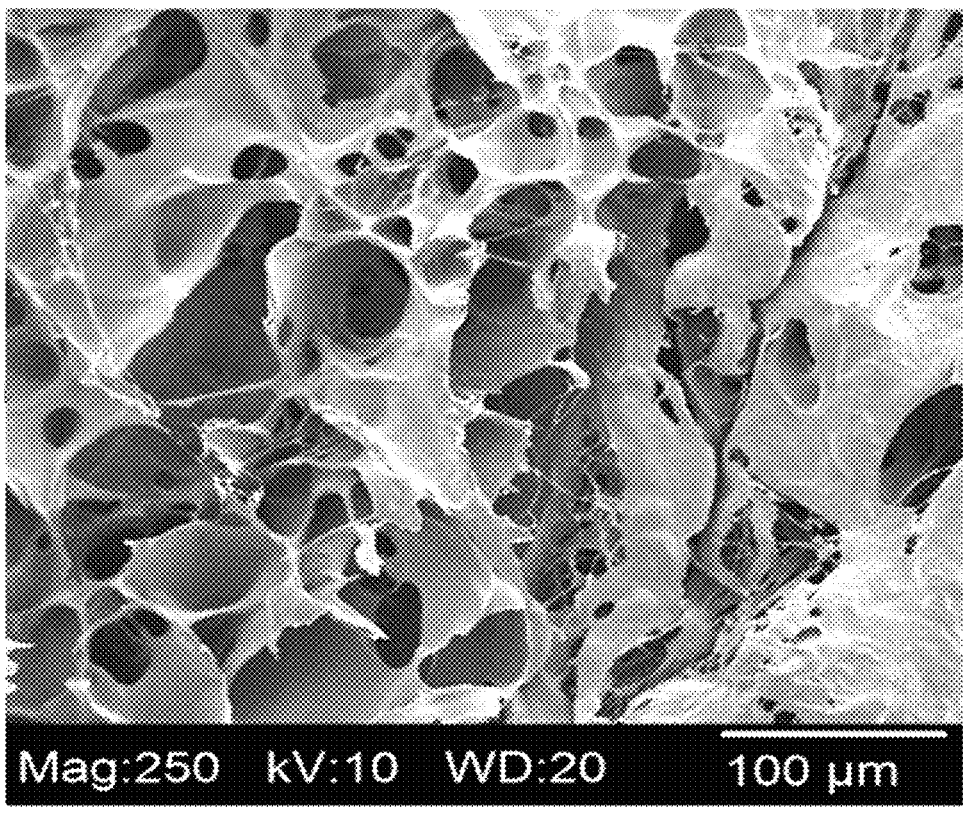
FIG. 3C is an electron micrograph of the bottom surface of the embodied collagen meniscus implant.
Figure 3D:
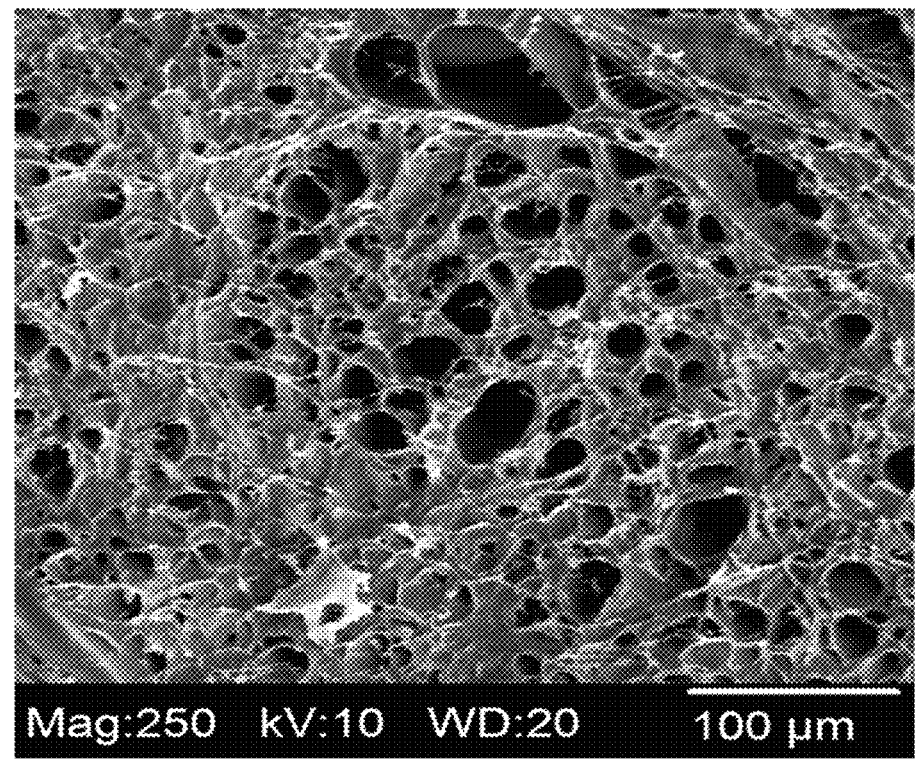
FIG. 3D is an electron micrograph of the perpendicular mid cross-section of the embodied collagen meniscus implant.
Figure 3E:
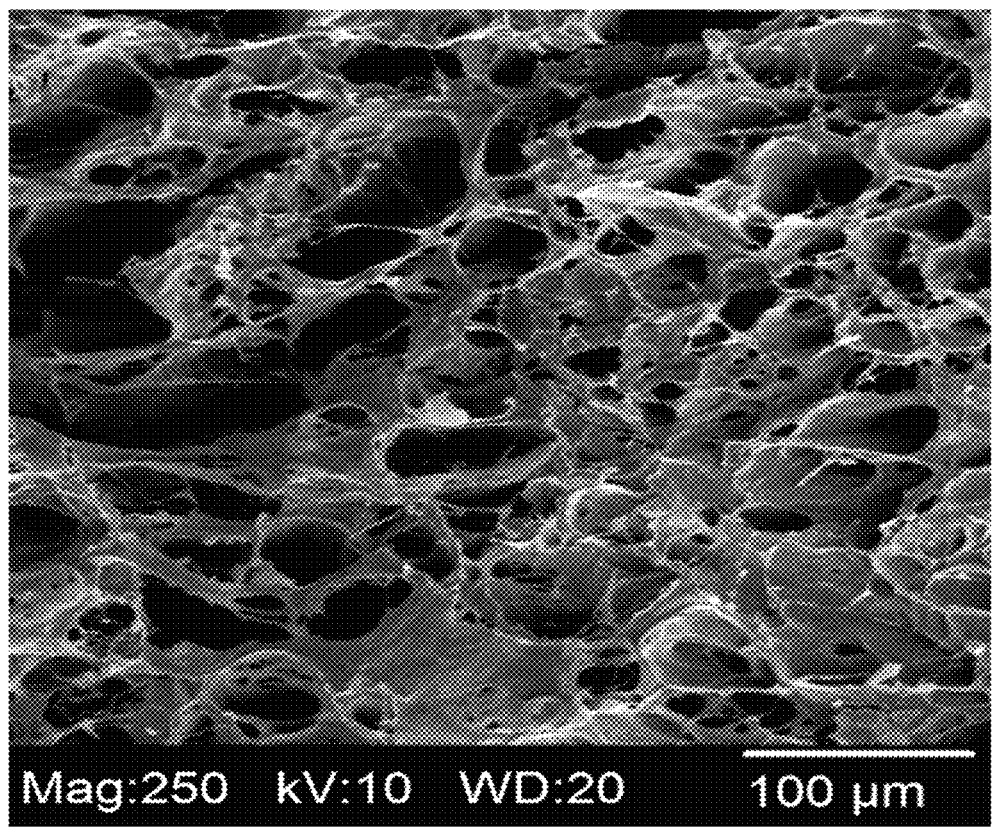
FIG. 3E is an electron micrograph of the parallel mid cross-section of the embodied collagen meniscus implant.

To guard against protein denaturation, machine shaping was performed at low temperature by briefly immersing the meniscus material in liquid $N_2$ prior to shaping. The immersion in liquid $N_2$ was repeated as needed throughout the machine shaping process. A machined meniscus sized to the dimension of a human medial meniscus is shown in FIG. 2. The dimensions of the medial meniscus after machining can be in the range of A=0.7-0.8 cm, B=3-4 cm, and H=0.5-0.6 cm, referring to the left side of FIG. 2. A lateral meniscus implant can be prepared as described above and machined to the appropriate size and shape for a human lateral meniscus. Referring to the right side of FIG. 2, the range of dimensions for the lateral meniscus after machining can be A=0.7-0.8 cm, B=2.5-3.5 cm, and H=0.5-0.6 cm.

The machined menisci were extracted in $H_2O$ overnight to remove water-soluble moieties. The washed menisci were extracted to remove non-collagenous moieties, cell debris, and DNA following established procedures for purifying xenogeneic tissues. See U.S. Pat. Nos. 5,681,353; 6,042,610; 6,599,524; 7,807,192; and 9,308,219. The extraction steps are described below.

The washed menisci were extracted in 0.2% sodium dodecyl sulfate (SDS) for 4 days, followed by extraction in 2% polyoxyethylene octylphenyl ether (TRITON™ X-100) for 3 days, to remove cell-associated non-collagenous materials including DNA and lipids. The menisci were then extracted in 3 M $MgCl_2$ for 48 h to remove proteoglycans and glycosaminoglycans, followed by extraction with 0.25 M NaOH in the presence of 1 M $Na_2SO_4$ for 6 h to remove alkaline soluble proteins and lipids. The alkaline treated menisci were then extracted in 0.2 M HCl in the presence of 0.5 M $Na_2SO_4$ for 18 h to remove acid soluble moieties. The inclusion of sodium sulfate in the acid and base extraction minimizes swelling of the menisci. The acid-treated menisci were extracted in 0.1 to 0.2 M NaCl for 18-24 h to remove neutral salt-soluble moieties. The salt treated menisci were rinsed in $H_2O$ for 18-24 h and then extracted in 100% isopropanol twice, first for 24 h and second for 8 h, to remove any residual lipids and alcohol soluble moieties. Finally, the purified menisci were washed in $H_2O$ and freeze-dried to yield the collagen meniscus implants. All extractions were performed at 4° C.

Prior to implantation, the freeze-dried collagen meniscus implant can be sterilized by gamma irradiation, either in a dry state or in a hydrated state.

Example 2: Chemical Analyses of Collagen Meniscus Implant

Chemical analyses were conducted to confirm the extent to which the non-collagenous moieties were removed during the above purification processes. These analyses are necessary to determine whether the collagen menisci are suitable for implantation in humans.

Hydroxyproline Analysis

Hydroxyproline analysis was performed to assess the total collagen content of the purified menisci. The hydroxyproline content was analyzed as described previously. See Bergman et al., Analytical Chemistry 35:1961-1965, 1963.

Briefly, desiccated samples of the collagen meniscus implants were weighed before being acid-hydrolyzed in 6 N HCl at 105° C. for 20 h in sealed glass tubes. The hydrolyzed samples were transferred to 50 mL volumetric flasks. To each sample, 3 mL of 1 N NaOH, 5 ml of citrate acetate buffer, and purified $H_2O$ were added to the line on the volumetric flask. A set of hydroxyproline standards was prepared to construct a standard curve. Each sample and standard (1 mL) was transferred to a glass test tube, and 1 ml each of 0.03 M chloramine T, 3 M perchloric acid, and 5% p-dimethylamino-benzaldehyde (DABA) was added to each tube. The samples and standards were incubated for 20 min. at 60° C. The optical density at 555 nm ($OD_{555}$) of the samples and standards were read in a spectrophotometer. The weight of hydroxyproline was calculated as the $OD_{555}$ of the sample divided by the slope of the standard curve and multiplied by any dilution factor. The percent hydroxyproline was calculated as the hydroxyproline weight obtained divided by the dry weight of the collagen meniscus implant sample multiplied by 100.

As mentioned above, the majority (>95%) of collagen in meniscus tissue is type I collagen. The measured hydroxyproline content of the implants was converted to collagen content under the assumption that the collagen contains 13% by weight of hydroxyproline.

DNA Analysis

Residual DNA was determined by a colorimetric method adapted from Gendimenico, G., et al. (Anal Biochem, 173: 45-8, 1988). In brief, 0.05 g of desiccated collagen meniscus implants were weighed and minced before centrifugation in 1 mL of 0.5 M perchloric acid for 10 min. at 800×g. The supernatant was discarded and the pellet was further treated in 1 mL of 0.5 M perchloric acid for 30 min. at 90° C. These hydrolyzed samples were centrifuged for 10 min. at 800×g. Diphenylamine reagent was added to 0.5 mL aliquots of each of the supernatants, as well as to a set of standards. The samples and standards were incubated at 50° C. for 4 h. The $OD_{600}$ of the samples and standards were read in a spectrophotometer. The percent DNA was calculated based on the slope of the standard curve, the volume of the solution, and the dry weight of the sample.

Amino Sugar Analysis

Amino Sugar content was determined by the method of Cleland, R. L., and Sherblom, P. J. (J. Biol. Chem., 252:2: 420-426, 1977). Desiccated samples of the collagen meniscus implants were weighed and hydrolyzed in 12 N HCl in a boiling $H_2O$ bath for 2 h. The samples were diluted with $H_2O$ and phenolphthalein indicator. The samples were neutralized with 6 N NaOH until a color change was observed, and then slowly back titrated with 1 N HCl until the color disappeared. A set of glucosamine standards were also prepared. Acetylacetone in sodium carbonate was added to each sample and standard and allowed to react in a boiling $H_2O$ bath for 30 min. At the end of the reaction, the samples and standards were transferred to volumetric flasks. Ethyl alcohol and DABA were added and the samples diluted to the line in the volumetric flasks with purified $H_2O$. After 30 min., the $OD_{530}$ of the samples was determined spectrophotometrically.

The percent amino sugar content was calculated using the slope of the glucosamine standard curve, the volume of solution, and the dry weight of the sample. Amino sugars are mostly associated with GAGs, including chondroitin-4 sulfate, chondroitin-6 sulfate, dermatan sulfate, and keratin sulfate. The amino sugar content was converted to GAG content assuming that the amino sugar content in the GAGs was 60% by weight.

SDS Polyacrylamide Gel Electrophoresis

The types and relative distribution of different collagens in the meniscus implants were analyzed by SDS polyacrylamide gel electrophoresis (SDS-PAGE) analysis.

Meniscus implant samples of 35 mg were minced and each dispersed in 0.5 M acetic acid in the presence of 3.5 mg of pepsin. The samples were digested for 48 h at room temperature. At the completion of the digestion, samples were neutralized to a pH range of 5-7. The resulting solutions were centrifuged and the supernatants incubated with Laemmli buffer/β-mercaptoethanol for 1 hour at 65° C. An SDS-PAGE gel (4-12% Bis-Tris) was loaded with 20-40 μL of the heated digested collagen meniscus implant samples, as well as protein standards. The gel was run at 200 V for 90 min. Proteins in the gel were visualized by Coomassie G250 stain following standard procedures.

The results of the chemical analyses are shown in Table 1 below.

TABLE 1

Chemical analyses of collagen meniscus implants

| Test Performed | Samples | Average ± S.D. | Comment |
|---|---|---|---|
| Hydroxyproline content | 6 | 12.8 ± 0.3% | 98.5 ± 2.3% of collagen in the sample (w/w) |
| DNA content | 6 | 0.0086 ± 0.0004% | 86 ± 5 ppm |
| Amino-sugar content | 6 | 0.047 ± 0.014% | 0.08 ± 0.02% of GAGs in the sample (w/w) |
| SDS PAGE | | Not applicable | Contains mostly type I collagen with minor amounts of type III collagen |

The results showed that greater than 98% by weight of the collagen meniscus implant was collagen. The purity of the collagen meniscus implant is comparable to purified bovine tendon collagen that has been in clinical use since 2001. See, e.g., RCM6® Resorbable Collagen Membrane, marketed by Ace Surgical, Brockton, MA.

The DNA content of the collagen meniscus implant, i.e., 86 ppm, was only slightly higher than the highly purified bovine tendon collagen mentioned above that has been used in clinical applications in over one million patients without any tissue related adverse reactions.

Turning to the GAG content, the measured amino sugar content of 0.047% by weight of the collagen meniscus implant corresponds to a total GAG content of about 0.08%. GAGs are concentrated mostly in the inner rims of meniscus tissue. Removal of the inner rims during the shaping procedure described above ensured that the residual GAG content was low.

Raw meniscus tissue contains mainly type I, type II, and type III collagens. It has been previously demonstrated that a majority of the type II collagen is located in the inner rim of the raw meniscus (see Cheung, H. S., 1987, Connective Tiss. Res. 16:343-356). In the above method, most of the inner rim was removed during the shaping step such that the purified collagen meniscus implant does not contain any significant amount of type II collagen. SDS-PAGE analysis demonstrated that the purified collagen meniscus implant contains a detectable amount of type III collagen.

Example 3: Physical Properties of Collagen Meniscus Implants

Collagen meniscus implants must have certain physical properties in order to be clinically useful in vivo. The density, pore volume, pore size, pore size distribution, tensile strength, suture retention strength, and hydrothermal stability were determined for the collagen meniscus implant using the methods set forth, infra.

Density

The density of the collagen meniscus implant was determined by measuring its volume and dry weight. The total volume of the implant is the sum of the volume occupied by the solid portions of the implant and the volume of the implant voids, as determined by water content (see below). The volume of the solid portions of the collagen meniscus implant was calculated based on the density of collagen, i.e., 1.41 g/cm³.

Water Content

Water content provides information on the pore volume of the collagen meniscus implant. The implant was fully hydrated in $H_2O$. The surface $H_2O$ was removed and the wet weight was determined. The hydrated implant was dried under $P_2O_5$ for 48 h and the dry weight determined. The water content was calculated as the weight difference between the wet weight and dry weight of the implant, divided by the dry weight of collagen.

Pore Sizes and Pore Size Distribution

The pore size and pore size distribution of the collagen meniscus implant was measured from scanning electron micrographs obtained at 250× magnification. ImageJ software (NIH) was used to measure in micrometers the widest distance across each measured pore.

Tensile Strength

A dumbbell shaped die punch was used to cut along the longitudinal direction of the collagen meniscus implant. The cut implant was further shaped into a rectangle and the cross-sectional area determined. The sample was then clamped at both ends of a mechanical tester (Lloyd LF Plus, Lloyd Instruments, LTD, United Kingdom). The sample was pulled along its longitudinal direction at a rate of one inch per minute until it broke or exceeded the load capacity of the instrument. The ultimate tensile strength, expressed in units of kg/cm², is the strength at which the sample breaks or exceeds the load capacity and the tensile modulus defined.

Suture Retention Strength

Suture retention strength is critical, as implantation of the collagen meniscus requires suturing it into the recipient meniscal rim to provide blood supply and to facilitate cell ingrowth into the implant. A one centimeter wide section the meniscus implant was removed by cutting along its radial direction with a scalpel. A needle attached to a 3-0 suture was passed through the implant at 3 mm from the back of the test sample. The sample was then attached to the mechanical tester mentioned above and the suture was pulled at a rate of one inch per minute until it was pulled out or exceeded load capacity. The suture pull-out strength is expressed in units of kg.

Hydrothermal Stability

The hydrothermal stability ($T_s$) was determined by a measurement of the thermal transition temperature of a hydrated collagen meniscus implant. A thin sample was sliced with a scalpel and a circular punch was taken from the sample and weighed. The sample was hydrated in phosphate buffer (pH 7.4), sealed in an aluminum cell, placed in a differential scanning calorimeter (Mettler-Toledo, Inc. Columbus, OH), and heated at a rate of 1° C./min. The $T_s$ is the temperature at which the transition from the triple helical structure of collagen to a random coil structure begins.

The results are shown in Table 2 below.

TABLE 2

Physical properties of the collagen meniscus implant

| Test | Number of Samples | Average ± S.D. |
|---|---|---|
| Density (g/cm³) | 5 | 0.29 ± 0.01 |
| Water Content (g/g) | 5 | 2.84 ± 0.08 |
| SEM | Not applicable | Pore sizes are in the range of 5 to 100 μm (See FIGS. 3A-E) |
| Tensile Strength (kg/cm²) | 4 | >650 |

TABLE 2-continued

| Physical properties of the collagen meniscus implant | | |
|---|---|---|
| Test | Number of Samples | Average ± S.D. |
| Suture Retention Strength (kg) | 4 | >3 |
| Hydrothermal Stability (° C.) | 4 | 56.9 ± 0.5 |

The density of the collagen meniscus implant was 0.29 g/cm³, a density within the range of that required of an implantable collage-based material. The water content measurement indicated that greater than 70% of the collagen meniscus implant is occupied by pores. SEM micrograph (see FIGS. 3A-E) measurements showed that the range of pores of the meniscus implant varied from 5 μm to about 100 μm. A significant number of pores were larger than cells, which are typically in the range of 20-30 μm. Thus, the pore sizes are in the range suitable for cell infiltration. Some of the pores appear interconnected in certain cross sectional views. Interconnection of the pores also facilitates cell migration into the implant.

The tensile strength of the implant in the longitudinal direction was high, exceeding the maximum strength registrable by the equipment, i.e., greater than 650 kg/cm². The suture retention strength of the implant along its radial direction was also high, registered at greater than 3 kg, an amount sufficiently high to ensure that the implant, once sutured in place, would not tear or detach from the suture site.

Hydrothermal stability is a parameter related to the in vivo stability of an implant. The higher the hydrothermal stability, the slower the rate of resorption of the implant in vivo. The hydrothermal stability of the collagen meniscus implant thus obtained is comparable to other collagen products having an in vivo stability of 6 months.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. A method for producing a collagen meniscus implant, the method comprising:
   obtaining a freshly excised non-human meniscus,
   rinsing the non-human meniscus in an aqueous solution,
   drying the rinsed non-human meniscus,
   shaping the dried non-human meniscus to the dimensions of an average-sized human meniscus,
   extracting the shaped non-human meniscus to remove non-collagenous material, and
   sterilizing the extracted non-human meniscus, thereby forming the collagen meniscus implant,
   wherein the collagen meniscus implant contains 81 to 91 ppm DNA; and the method is free of any enzymatic digesting steps and oxidizing steps.

2. The method of claim 1, wherein the collagen meniscus implant has a density of about 0.29 g/cm³, contains at least 90% by weight of type I collagen, and less than 0.2% by weight of glycosaminoglycan.

3. The method of claim 1, wherein the collagen meniscus implant has a void volume of at least 60% of the total implant volume.

4. The method of claim 1, wherein the collagen meniscus implant is biocompatible with a human patient.

5. The method of claim 1, wherein the collagen meniscus implant is bioresorbable and is stable in vivo after implantation for a period of 6 to 12 months.

6. The method of claim 1, wherein the non-human meniscus is bovine meniscus.

* * * * *